United States Patent [19]

Illy et al.

[11] Patent Number: 4,692,540

[45] Date of Patent: Sep. 8, 1987

[54] PROCESS FOR THE PREPARATION OF CYCLIC PHOSPHITES

[75] Inventors: Hugo Illy, Reinach, Switzerland; Björn Schliebs, Lindenfels-Glattbach; Wilhelm Hess, Jugenheim, both of Fed. Rep. of Germany

[73] Assignee: Ciba-Geigy Corporation, Ardsley, N.Y.

[21] Appl. No.: 723,115

[22] Filed: Apr. 15, 1985

[30] Foreign Application Priority Data

Apr. 17, 1984 [CH] Switzerland ................... 1945/84
Jun. 26, 1984 [CH] Switzerland ................... 3066/84

[51] Int. Cl.$^4$ .............................................. C07F 9/15
[52] U.S. Cl. .................................................. 558/78
[58] Field of Search ................ 260/976, 973; 558/95, 558/96, 78

[56] References Cited

U.S. PATENT DOCUMENTS

| | | | |
|---|---|---|---|
| 3,192,243 | 6/1965 | Gagliani | 260/976 |
| 3,689,602 | 9/1972 | Ismail | 260/976 |
| 3,968,188 | 7/1976 | Birum et al. | 558/77 |
| 4,312,818 | 1/1982 | Maul et al. | 260/976 |

FOREIGN PATENT DOCUMENTS 485120 9/1975 U.S.S.R. .
550399 5/1977 U.S.S.R. .

*Primary Examiner*—Anton H. Sutto
*Attorney, Agent, or Firm*—Harry Falber

[57] ABSTRACT

The present invention relates to a process for the preparation of pentaerythritol esters of phosphorous acid derivatives by reacting pentaerythritol with a phosphorous trihalide and a phenol in the presence of a quaternary salt or a polyether.

The use of such catalysts is not only able to improve the yield, but also makes it possible for the entire process to be carried out in one step by adding the phenol at the start of the reaction of pentaerythritol with the phosphorous halide.

9 Claims, No Drawings

PROCESS FOR THE PREPARATION OF CYCLIC PHOSPHITES

The present invention relates to a novel process for the preparation of pentaerythritol esters of phosphorous acid derivatives.

The esterification of pentaerythritol with triphenyl phosphite and the subsequent esterification with dialkylphenols to give corresponding di(dialkylphenol)pentaerythritol diphosphites is generally known. It is also known that these products always contain phenol radicals which result in malodorous emissions. In U.S. Pat. No. 4,290,976 the proposal is made to eliminate phenols by preparing dialkylpentaerythritol diphosphites by reacting dichloropentaerythritol diphosphite with alkanols. Moreover, large amounts of suitable acid acceptors such as amines and alkali salts are used for neutralising hydrogen chloride. In the preparation of dichloropentaerythritol diphosphite as described e.g. in U.S. Pat. No. 3,192,242, however, by-products form which are difficult to separate. According to U.S. Pat. No. 3,968,188, the formation of such troublesome by-products can be substantially inhibited by carrying out the reaction of pentaerythritol with $PCl_3$ in the presence of a metal halide or tertiary amine as catalyst.

Surprisingly, it has now been found that the yield can be improved considerably by catalysing the reaction of pentaerythritol with $PCl_3$ with a quaternary salt or a polyether. It has been found that, when using such a catalyst, the phenol can be added direct at the start of the reaction of pentaerythritol with the phosphorous trihalide and thus the corresponding diphenolpentaerythritol diphosphite can be obtained in one step.

Accordingly, the present invention relates to a process for the preparation of pentaerythritol esters of phosphorous acid derivatives of formula I

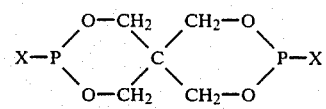

wherein X is chlorine, bromine, or a group of formula II

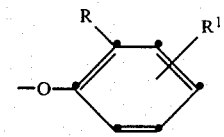

wherein each of R and $R_1$ independently of the other is hydrogen or $C_1$-$C_8$alkyl, by reacting pentaerythritol with a phosphorous trihalide, in an inert organic solvent, and, if X is a group of formula II, additionally with a phenol of formula III

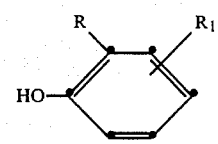

which process comprises carrying out the reaction in the presence of a catalyst selected from the group consisting of quaternary ammonium, phosphonium, arsonium, pyridinium, piperazinium and thiazolium salts, tertiary sulfonium salts, crown ethers and linear polyethers, in an amount of 0.5 to 20 mol%, based on pentaerythritol, said phenol of formula III being added at the start of, during or after the reaction of pentaerythritol with the phosphorous trihalide.

It is also possible to carry out the reaction of pentaerythritol with the phosphorous trihalide in the presence of one of the catalysts specified above to give the compound of formula I, wherein X is chlorine or bromine, which compound can subsequently be further reacted without being isolated, or to add the phenol of formula III at the start of or during the reaction of pentaerythritol with the phosphorous trihalide and thus obtain the compound of formula I, wherein X is a group of formula II, in one step.

If a solid phenol of formula III is used, it is preferable to place said phenol in the reaction flask before the other reactants, regardless of the fact whether the reaction of pentaerythritol with the phosphorous trihalide is carried out simultaneously or beforehand. A major advantage of the process of this invention is that the dihalide (compound of formula I, wherein X is chlorine or bromine), which is unstable in pure form, does not have to be isolated.

Accordingly, the process of this invention is of particular interest for the preparation of compounds of formula I, wherein X is chlorine or bromine. Chlorine is preferred.

The process of this invention is likewise of interest for the preparation of compounds of formula I, wherein X is a group of formula II, with the phenol being added at the start of the reaction of pentaerythritol with the posphorous trihalide.

Suitable phosphorous trihalides are e.g. $PBr_3$ and, in particular, $PCl_3$. The preferred molar ratio of phosphorous trihalide to pentaerythritol is about 2:1.

Examples of R and $R_1$ as $C_1$-$C_8$alkyl are methyl, ethyl, propyl, isopropyl, n-butyl, sec-butyl, tert-butyl, pentyl, hexyl, n-octyl, 2-ethylhexyl, 1,1,3,3-tetramethylbutyl. $R_1$ is preferably in the p-position to the oxygen atom. R is preferably branched $C_3$-$C_{10}$alkyl, most preferably tert-butyl, and $R_1$ is preferably methyl or tert-butyl.

The quarternary ammonium, phosphonium, arsonium, pyridinium, piperazinium, thiazolinium salts and the tertiary sulfonium salts, the crown ethers and the linear polyethers which are suitable as catalysts for the process of this invention are generally known as phase transfer catalysts and are commercially available, e.g. the following:

benzyldimethylhexadecylammonium chloride, benzyldimethyltetradecylammonium chloride, benzyldimethyltetradecylammonium bromide, benzyltributylammonium bromide, benzyltributylammonium chloride, benzyltriethylammonium bromide, benzyltriethylammonium chloride, benzyltriethylammonium iodide, benzyltriethylammonium tetrafluoroborate, benzyltrimethylammonium bromide, benzyltrimethylammonium chloride, benzyltrimethylammonium hydroxide, benzyltriethylammonium hydroxide, benzyltrimethylammonium methoxide, benzyltriphenylphosphonium bromide, bis(tetramethylammonium) sulfate, butyltriphenylphosphonium bromide, butyltripropylammonium bromide, 12-crown-4, 15-crown-5, 18-crown-6, dibenzo-18-crown-6, dibenzo-24-crown-8, dicyclohexano-18-crown-6, dicyclohexano- 24-crown-8, diethylmethylpropylammonium bromide, (diisobutylcresoxyethoxyethyl)dimethylbenzylammonium chloride, (diisobutylphenoxyethoxyethyl)dimethylbenzylammonium chloride, dimethylethyldodecylammonium bromide, dimethylethylhexadecylammonium bromide, dimethylethylpropylammonium bromide, 3,4-dimethyl-5-(2-hydroxyethyl)-thiazolium iodide, 1,1-dimethyl-4-phenylpiperazinium iodide, dimethyl tetraglycol, dodecylethyldimethylammonium bromide, 1-butylpyridinium bromide, 1-heptylpyridinium bromide, 1-dodecylpyridinium bromide, decyltriethylammonium bromide, hexadecyltriethylammonium bromide, hexadecyltrimethylammonium bromide, ethyldimethylpropylammonium bromide, ethylhexadecyldimethylammonium bromide, 3-ethyl-5-(2-hydroxyethyl)-4-methylthiazolium bromide, ethyltriphenylphosphonium bromide, heptyltributylammonium bromide, hexadecylpyridinium bromide, hexadecylpyridinium chloride, hexyltriethylammonium bromide, hexadecyltributylphosphonium bromide, hexadecyltrimethylammonium bromide, hexadecyltrimethylammonium chloride, 2-hydroxyethyltrimethylammonium chloride, 2-hydroxyethyltrimethylammonium chloride, 2-hydroxyethyltrimethylammonium hydroxide, 2-hydroxyethyltrimethylammonium iodide, methyltributylammonium bromide, methyltributylammonium chloride, methyltributylammonium hydroxide, methyltributylammonium iodide, methyltriethylammonium bromide, methyltrioctylammonium bromide, methyltrioctylammonium chloride, methyltrioctylammonium iodide, methyltriphenylphosphonium bromide, octadecyltrimethylammonium bromide, pentyltributylammonium bromide, phenyltrimethylammonium bromide, phenyltrimethylammonium chloride, phenyltrimethylammonium hydroxide, phenyltrimethylammonium tribromide, octyltriethylammonium bromide, tetrabutylammonium acetate, tetrabutylammonium borohydride, tetrabutylammonium bromide, tetrabutylammonium chloride, tetrabutylammonium cyanate, tetrabutylammonium cyanide, tetrabutylammonium cyanoborohydride, tetrabutylammonium dichromate, tetrabutylammonium fluoride trihydrate, tetrabutylammonium hexafluorophosphate, tetrabutylammonium hydrogensulfate, tetrabutylammonium hydroxide, tetrabutylammonium iodide, tetrabutylammonium methanesulfonate, tetrabutylammonium nitrate, tetrabutylammonium nitrite, tetrabutylammonium perchlorate, tetradecyltriethyla mmonium bromide, tetradodecylammonium bromide, tetradodecylammonium perchlorate, tetraethylammonium acetate tetrahydrate, tetraethylammonium borohydride, tetraethylammonium bromide, tetraethylammonium chloride monohydrate, tetraethylammonium cyanide, tetraethylammonium fluoride dihydrate, tetraethylammonium hexafluorophosphate, tetraethylammonium hydrogensulfate, tetraethylammonium hydroxide, tetraethylammonium iodide, tetraethylammonium nitrate, tetraethylammonium perchlorate, tetraethylammonium tetrafluorborate, tetraethylammonium thiocyanate, tetraheptylammonium bromide, tetrahexylammonium bromide, tetrahexylammonium chloride, tetrahexylammonium iodide, tetrahexylammonium perchlorate, tetramethylammonium bromide, tetramethylammonium chloride, tetramethylammonium hexafluorophosphate, tetramethylammonium hydroxide, tetramethylammonium iodide, tetramethylammonium nitrate, tetramethylammonium perchlorate, tetramethylammonium sulfate, tetramethylammonium tetrafluoroborate, tetramethylammonium tribromide, tetraoctadecylammonium bromide, tetraoctylammonium perchlorate, tetrapentylammonium bromide, tetrapentylammonium iodide, tetraphenylarsonium chloride, tetrabutylphosphonium chloride, tetraphenylphosphonium bromide, tetraphenylphosphonium chloride, trioctylethylphosphonium bromide, tetrapropylammonium bromide, tetrapropylammonium hydroxide, tetrapropylammonium iodide, tributylheptylammonium bromide, tributylhexadecylphosphonium bromide, tributylmethylammonium bromide, tributylmethylammoniumm chloride, tributylmethylammonium hydroxide, tributylmethylammonium iodide, tributylpentylammonium bromide, triethylmethylammonium bromide, trimethyloctadecylammonium bromide, trimethylphenylammonium bromide, trimethylphenylammonium chloride, trimethylphenylammonium tribromide, trimethyltetradecylammonium bromide, trioctylmethylammonium chloride, tripropylbutylammonium bromide, tetraethyleneglycol dimethyl ether, 1,4,7,10-tetraoxacyclododecane.

Preferred catalysts are quaternary ammonium or phosphonium salts of the formula IV or V

    (IV)

    (V)

wherein $R_2$ is $C_1$–$C_8$ alkyl, $R_3$ is phenyl, Y is chlorine or bromine, and n is from 0 to 4.

$R_2$ as $C_1$–$C_8$ alkyl is e.g. methyl, ethyl, propyl, isopropyl, n-butyl, sec-butyl, tert-butyl, pentyl, hexyl, oxtyl, with straight chain alkyl being preferred, in particular ethyl and n-butyl.

n is preferably 1, and Y is preferably bromine.

Particularly preferred catalysts are butyltriphenylphosphonium bromide and, in particular, tetraethylammonium bromide and tetrabutylammonium bromide.

The catalyst is preferably used in amounts from 1 to 10 mol%, in particular from 1.5 to 7 mol%, based on pentaerythritol, in the temperature range from 20° to 100° C., preferably from 30° to 80° C., under normal or reduced pressure for 2 to 9 hours.

If the reaction with the phenol or formula III is not carried out until after the formation of the compound of formula I, wherein X is chlorine or bromine, then further reaction is preferably carried out using the same catalyst.

Suitable solvents are e.g. aromatic hydrocarbons such as benzene, toluene and, in particular, xylene, or mixtures of aliphatic and aromatic hydrocarbons.

The working up of the resultant product is effected by conventional methods.

The compounds of formula I, wherein X is a group of formula II, are valuable stabilisers for organic materials which are subject to decomposition, preferably for synthetic polymers.

The invention is illustrated by the following non-limitative Examples.

EXAMPLE 1

A 2 liter reaction flask equipped with an HCl absorber is charged with 95.4 g (0.7 mol) of pentaerythritol, 4.8 g (0.014 mol) of tetrabutylammonium bromide and 240 g of toluene. The suspension is thoroughly stirred and heated to about 40° C. while introducing nitrogen. 200 g (1.45 mol) of phosphorous trichloride are then added dropwise over 3 to 3½ hours at regular intervals and the reaction mixture is stirred further for one hour at 38° to 40° C. The temperature is then increased over one hour to 65° C. and stirred for a further two hours at 65° to 70° C. Subsequently, about 45 g of toluene and traces of excess phosphorous trichloride are distilled off under a vacuum of 200 to 150 mbar. The amount distilled off is replaced by the same amount of fresh toluene.

The clarified solution is heated to 65° to 70° C. and, at this temperature, a solution of 302 g (1.146 mol) of 2,4-di-tert-butylphenol in 100 g of toluene is added dropwise over one hour and the reaction mixture is stirred further for one hour. Subsequently, about 250 g of toluene are distilled off under a low vacuum and replaced by 365 g of isopropanol. The resultant crystalline suspension is filtered at room temperature and the filter cake is washed with isopropanol on the filter and dried in vacuo, affording 340 g of 3,9-bis(2,4-di-tert-butylphenoxy-2,4,10-tetraoxa-3,9-diphosphaspiro[5.5]undecane with a melting point of 178° to 179° C.

EXAMPLE 2

40.8 g (0.3 mol) of pentaerythritol, 123.8 g (0.6 mol) of 2,4-di-tert-butylphenol and 3 g (0.014 mol) of tetraethylammonium bromide in 45 ml of xylene are suspended in a 500 ml reaction flask equipped with an HCl absorber. At 15° to 25° C., 82.3 g (0.6 mol) of phosphorous trichloride are added uniformly over one hour. The temperature is then raised uniformly over two hours to 70° C. Subsequently, a pressure of 120 mbar is applied. Pressure and temperature are maintained for two hours. 200 ml of xylene are then added to dissolve the product of 80° C. The solution is filtered in a distillation flask and the filter residue is washed with 2×50 ml of xylene. At 80° C. and 120 mbar, about 300 ml of xylene are distilled off until the limit of stirrability is reached. Then 400 ml of isopropanol are added rapidly and the suspension is stirred under reflux for 15 minutes at 80° C., then cooled to 20° to 25° C. The product is filtered and washed with 2×70 ml of isopropanol. The filter cake is dried in vacuo at 70° C., affording 133.3 g of 3,9-bis(2,4-di-tert-butylphenoxy)2,4,8,10-tetraoxa-3,9-diphosphaspiro[5.5]undecane with a melting point of 174° to 177° C.

What is claimed is:

1. A process for the preparation of a pentaerythritol ester of a phosphorous acid derivative of formula I

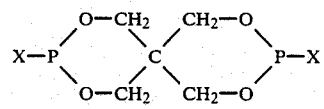

wherein X is chlorine, bromine, or a group of formula II

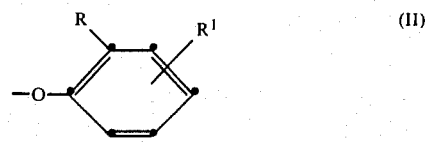

wherein each of R and $R_1$ independently of the other is hydrogen or $C_1$-$C_8$alkyl, by reacting pentaerythritol with a phosphorous trihalide, in an inert organic solvent, and, if X is a group of formula II, additionally with a phenol of formula III

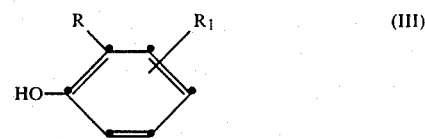

which process comprises carrying out the reaction in the presence of a catalyst selected from the group consisting of quaternary ammonium, phosphonium, arsonium, pyridinium, piperazinium and thiazolium salts, tertiary sulfonium salts, crown ethers and linear polyethers, in an amount of 0.5 to 20 mol%, based on pentaerythritol, said phenol of formula III being added at the start of, during or after the reaction of pentaerythritol with the phosphorous trihalide.

2. A process according to claim 1, wherein X in formula I is chlorine or bromine.

3. A process according to claim 1, wherein X in formula I is a group of formula II, and the phenol of formula III is added at the start of the reaction of pentaerythritol with the phosphorous trihalide.

4. A process according to claim 1, wherein the phosphorous trihalide is $PCl_3$.

5. A process according to claim 3, wherein $R_1$ in formulae II and III is in the p-position to the oxygen atom, and R and $R_1$ in formulae II and III are tert-butyl.

6. A process according to claim 1, wherein the catalyst is an ammonium or phosphonium salt of formula IV or V $$(R_2)_4N^\oplus Y^\ominus \quad \text{(IV)}$$
$$(R_2)_nP^\oplus(R_3)_{4-n}Y^\ominus \quad \text{(V)}$$

wherein $R_2$ is $C_1$-$C_8$alkyl, $R_3$ is phenyl, Y is chlorine or bromine, and n is from 0 to 4.

7. A process according to claim 6, wherein $R_2$ is ethyl or butyl.

8. A process according to claim 7, wherein n is 1, and Y is bromine.

9. A process according to claim 1, wherein the reaction is carried out in the presence of tetraethylammonium bromide or tetrabutylammonium bromide.

* * * * *